United States Patent [19]

Lakatos et al.

[11] Patent Number: 4,997,419
[45] Date of Patent: Mar. 5, 1991

[54] LAPAROSCOPY CANNULA

[75] Inventors: Nicholas Lakatos, Des Plaines; Boris Gluzerman, Chicago; Paul W. Hensler, Lake Bluff, all of Ill.

[73] Assignee: Edward Weck Incoporated, Princeton, N.J.

[21] Appl. No.: 359,595

[22] Filed: Jun. 1, 1989

[51] Int. Cl.$^5$ .................. A61B 17/34; A61M 31/00
[52] U.S. Cl. .................. 604/55; 604/164; 606/190
[58] Field of Search ............ 604/164–170, 604/264, 55; 128/3, 4, 7, 6; 606/190

[56] References Cited

U.S. PATENT DOCUMENTS

| | | | |
|---|---|---|---|
| 2,212,484 | 8/1940 | Wolf | 128/7 |
| 2,487,498 | 11/1949 | Wallace | 128/7 |
| 2,708,437 | 5/1955 | Hutchins | 128/7 |
| 3,777,743 | 12/1973 | Binard et al. | |
| 4,474,576 | 10/1984 | Gobby | 604/264 X |
| 4,491,126 | 1/1985 | Cullor | 604/55 |
| 4,585,438 | 4/1986 | Makler | 604/55 X |
| 4,617,933 | 10/1986 | Hasson | 606/190 |
| 4,802,461 | 2/1989 | Cho | 128/7 |

Primary Examiner—Robert A. Hafer
Assistant Examiner—Kerry Owens
Attorney, Agent, or Firm—Robert E. Lee; Gene Warzecha

[57] ABSTRACT

A cannula for use in laparoscopy is provided which includes an elongated shaft with a lumen along its longitudinal axis and a tip having a lumen and a conical member for engaging the cervix. The tip includes a distal end portion which is transverse to the longitudinal axis of the shaft. The cannula includes a tenaculum clamp coupling which is movable along at least a portion of the shaft within a plane through the shaft. Means are provided for attaching the tip to the shaft with the transverse distal end portion being fixed at any desired location rotationally about the longitudinal axis. Alternatively, means are provided for aligning the transverse distal end portion with the plane of movement.

13 Claims, 6 Drawing Sheets

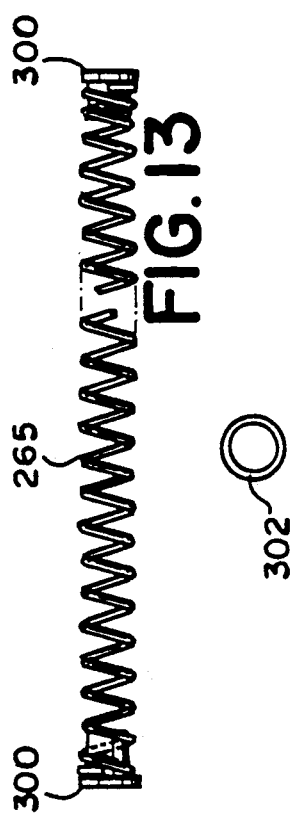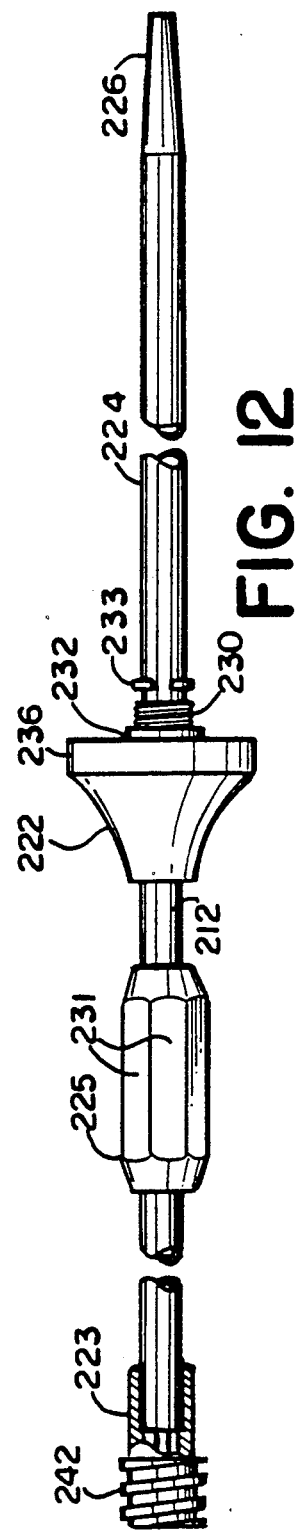

LAPAROSCOPY CANNULA

The present invention relates to improved instruments used in laparoscopy, particularly to an improved cannula used in combination with a cervical tenaculum.

When performing a laparoscopy to examine the uterus, ovaries and fallopian tubes, it is common procedure for the doctor to use a cervical tenaculum to manipulate the uterus through the vagina in elevating the uterus, moving it side to side, or flexing it retrograde to give the doctor a better view of the abdominal cavity through the laparoscope. During the procedure a cannula is often inserted through the vaginal canal and cervix into the uterus. The procedure requires the patient to lie on her back and the tenaculum is positioned anteriorly, i.e. uppermost, relative to the inserted cannula. The distal end of the tip of the cannula is transverse to the longitudinal axis of the remainder of the cannula at an angle of 27° and is positioned at the twelve o'clock position relative to rotation about the longitudinal axis, i.e. directed toward the tenaculum. See FIG. 9. A conical member spaced apart from the tip by a preselected amount is adapted to engage the cervix and seal off the uterine cavity.

The cannula includes a spring biased coupler which is adapted to slide along the cannula and couple to the handle portion of the tenaculum. The coupler includes a member which extends away from the cannula again at the twelve o'clock orientation to engage the handle section of the tenaculum thereby fixing the orientation of the cannula relative to the forceps. With the tenaculum properly positioned and the cannula coupled thereto, the transverse distal end of the tip of the cannula will be properly oriented within the uterus.

The cannula has a connector coupled to its proximal end coupling a source of liquid, for example, a dye, to the lumen of the cannula. The tip of the cannula includes at least one hole extending through the wall to the lumen in the tip which is in fluid communication with the lumen of the remainder of the cannula. The distance between the conical member and the holes (between two and three inches) places the holes near the connection points of the fallopian tubes within the uterus. When dye is injected into the uterus through the cannula it is forced up through the fallopian tubes (the cervix is sealed by the conical member) where it can be viewed through the laparoscope. The orientation of the transverse distal end of the tip of the cannula is very important to the success of the procedure.

In prior art cannula of this type, the tip assembly of the cannula including the conical member is coupled to the remainder of the cannula by means of a luer lock made from brass. The conical member is fixed in position on the tip. Repeated coupling and decoupling of the tip and conical member for cleaning or for changing size causes the soft brass to be stretched so that the transverse distal end of the tip is no longer at twelve o'clock. This causes a change in the doctor's technique since he must reposition the tenaculum to accommodate the change in the orientation of the tip relative to the coupling member in the cannula. This is undesireable since doctors are very uncomfortable with occurrences that require change in technique used in surgery.

During production of the cannulas the male/female luer connectors have to be dedicated to the main cannula body. This means that with hospitals having multiple inventories of the cannulas the tip and conical connection assemblies must be serialized or color coded because they cannot be mixed or matched with other main body assemblies, and where repair of the cannula is required a matched tip and conical connection assembly must be taken out of service.

SUMMARY OF THE INVENTION

The improved cannula of the present invention provides for an elongated shaft containing a lumen therethrough. A shaft tip is coupled to the distal end of the elongated shaft and includes a distal end portion transverse to the longitudinal axis of the cannula and a conical portion disposed to engage the cervix. The shaft tip has a lumen which is open to ambient atmosphere through at least one hole in the shaft tip. Means are provided for attaching the shaft tip to the elongated shaft such that the transverse distal end portion can be fixed at any rotational angle about the longitudinal axis of the elongated shaft.

The cannula also includes a coupling means which is movable along the elongated shaft within a plane through the shaft. The coupling means is movable against a biasing means which biases the coupling means towards the proximal end of the cannula. The coupling means extends away from the cannula within the plane and is adapted to engage a tenaculum used to seize the cervix through the vagina. Because the shaft tip can be attached to the elongated shaft at any rotational angle, the shaft tip can always be aligned with the plane of movement of the coupling means.

The cannula includes a connection at its proximal end for coupling a source of liquid or fluid to the cannula lumen.

The conical member is freely rotatable about the shaft tip and includes an internal threaded region which mates with an external thread found at the distal end of the elongated shaft. A retainer member attached to the proximal end of the shaft tip captures the conical member on the shaft tip between the proximal end and the transverse distal end portion. The retainer member is adapted to fit within a recess formed within the conical member distally of the internally threaded region of the conical member. The recess member contains a conically shaped recess adapted to receive a mating conical shape on the elongated shaft.

The external threads and the conical shape on the elongated shaft are present on a conical member connector attached to the distal end of the shaft.

Alternatively, the invention provides for attaching the shaft tip to the elongated shaft at a fixed rotational angle, as in the prior art, but including means for aligning the plane of the shaft tip with the plane of movement of the coupling means. The attaching means includes an annular washer fixed to the medial portion of the elongated shaft, an annular curved finger grip rotatably mounted on the shaft between the shaft tip and the washer and an elongated cylindrical sleeve which receives the proximal end of the shaft and attaches to the curved finger grip. The coupling means is attached to the sleeve and the elongated shaft with attached tip can be rotated relative to the sleeve and coupling means. The coupling means is disposed to slide back and forth along the sleeve with a fixed plane. The coupling means is biased toward the proximal end of the cannula. The surfaces of the cannula washer are bearing surfaces against which the curved grip and spring rotate when the shaft is rotated. The cannula further includes an elongated finger grip coaxial with and fixed to the shaft distally of the curved grip.

BRIEF DESCRIPTION OF THE DRAWINGS

FIG. 12 is an enlarged elevational plan view, partially in cross section, of a portion of the device in FIG. 11.

FIG. 13 is a plan view and end view of the spring used with the cannula of FIG. 10.

DETAILED DESCRIPTION OF THE DRAWINGS

Figure 1:
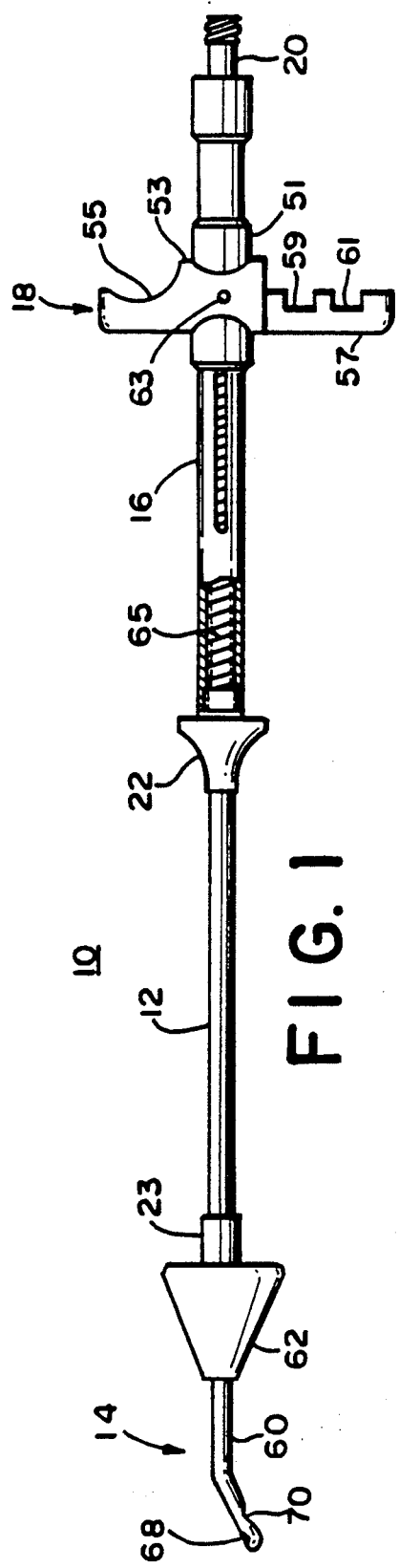
FIG. 1 is an elevational plan view, partially in cross section, of the laparoscopy cannula of the present invention.

Referring now to FIG. 1, the cannula designated generally 10 is shown having an elongated shaft 12, a shaft tip designated generally 14, sleeve 16, a coupler designated generally 18, proximal connector 20, finger grip 22 and a portion of a second connector 23.

Figure 2:
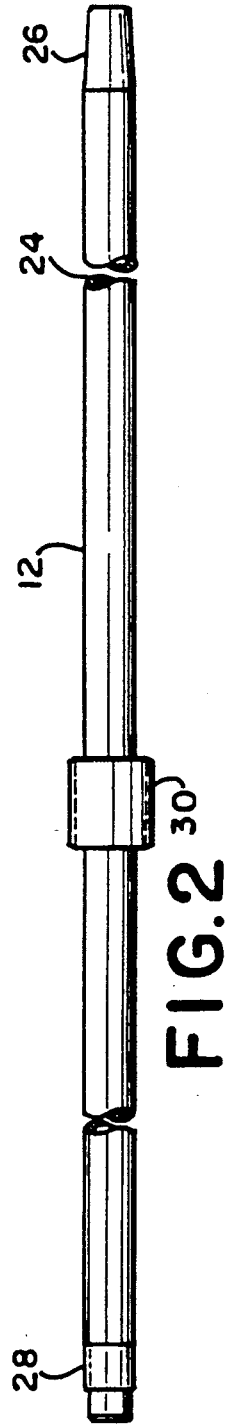
FIG. 2 is an enlarged elevational plan view of an elongated shaft portion of the cannula of FIG. 1.

FIG. 2 shows the elongated shaft 12 enlarged and in more detail. It is preferably made of stainless steel, cylindrical in shape, straight and includes a central lumen 24 which is open to ambient atmosphere at each end. End 26 is tapered while end 28 includes an external threaded region spaced apart from the tip. An externally threaded bushing 30 is positioned on the shaft 12 in the center region of the shaft.

Figure 3:
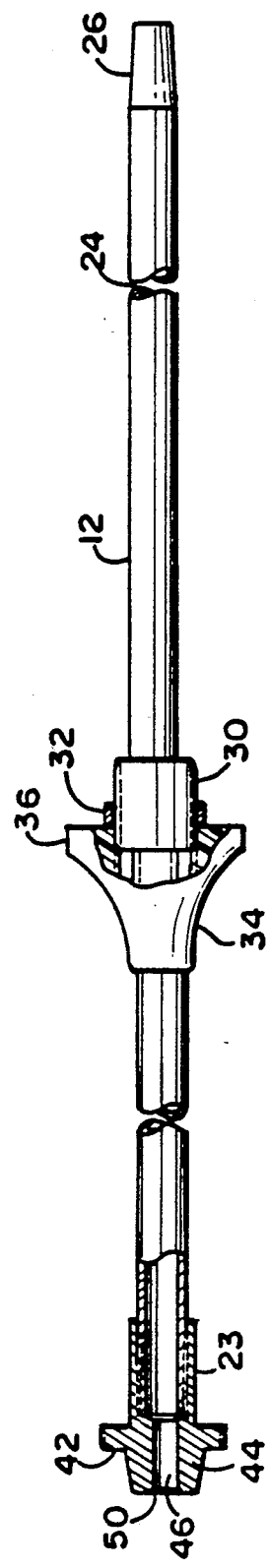
FIG. 3 is an elevational plan view of the shaft portion of FIG. 2 having a distal end connector shown in cross section.

FIG. 3 shows the shaft 12 of FIG. 2 with an annular stop ring 32 threaded onto the externally threaded bushing 30 and positioned in the center region of the bushing. Concave curved, annularly shaped finger grip 22 has a center through hole large enough to accommodate the shaft 12 and is positioned on the shaft 12. An internally threaded bore within the base 36 of the finger grip 22 mates with the threads on the bushing 30. The grip 22 is threaded onto the bushing 30 until it engages the stop ring 32.

Figure 4:
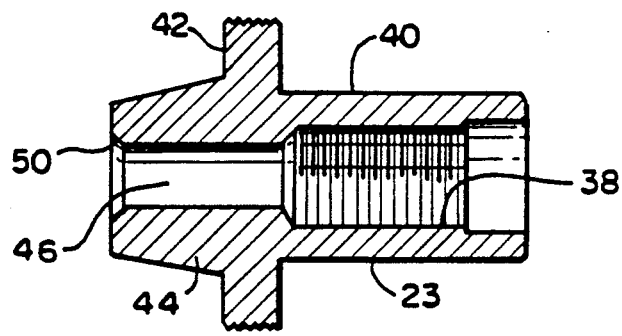
FIG. 4 is an enlarged cross sectional view of the connector of FIG. 3.

FIG. 3 along with FIG. 4 shows the second connector 23 of FIG. 1 in cross section attached to the end of the elongated shaft 12. The connector 23 is generally cylindrical in shape with a bore 38 in a proximal body portion 40 with internal threads to mate with the external threads at 28 on the shaft 12. The connector further includes an externally threaded annular ring 42 having a larger diameter than the remainder of the connector but integrally formed therewith. Finally, the distal end portion 44 of the connector is conically shaped. The bore 38 communicates with a lumen 46 through the connector which is open to ambient atmosphere at the connector's distal end and which serves to extend the lumen 24 of the shaft 12 through the connector 23. The lumen 46 is of smaller diameter than the shaft lumen 24. Where the lumen 46 opens to ambient atmosphere it includes an enlarging taper 50. The connector 23 is threaded onto the end of the shaft after end 28 of the shaft is passed through the finger grip 22.

Figure 5:
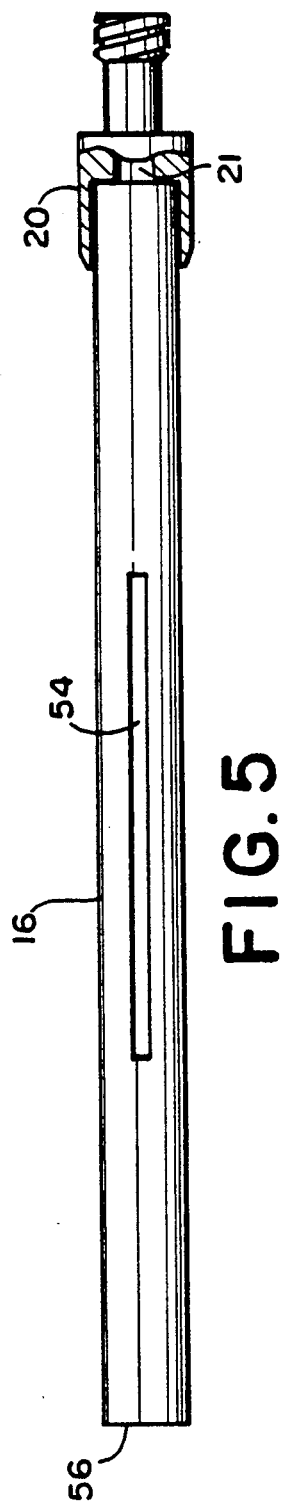
FIG. 5 is an enlarged elevational plan view of a sleeve portion of the cannula of FIG. 1 having a proximal end connector shown partially in cross section.

Referring now to FIG. 5, the sleeve 16 and proximal connector 20 (shown partially is cross section) are shown in more detail. The sleeve is a straight, hollow metallic cylinder (stainless steel is preferred) having a pair of diametrically opposed, elongated slots 54. The internal diameter of the sleeve is constant and is large enough for the distal end of the sleeve 56 to be threaded onto the bushing 30 until the distal end of the sleeve contacts the stop ring 32. The opposite end of sleeve 16 is inserted into a bore in the connector 20 and attached by soft solder. In the preferred embodiment, the connector 20 is a male luer lock connector. The bore of the connector is in communication with a tapered interior bore portion 21 which accepts the conically tapered end 26 of the shaft 12 when the sleeve is assembled over the shaft.

Referring to FIG. 1, the coupler 18 comprises a hollow cylindrical tube 51 through which the sleeve 16 is inserted. The tube passes through a hole in a second tube member 53 at right angles thereto. The second tube member 53 has a first portion with a concave cut out 55 which extends away from the first tube in a first direction and a flat portion 57 which extends away from the first tube in a second opposite direction from the first portion in a common plane therewith. The flat portion includes notches 59 and 61. Pins 63 extend through both the second and first tube members through opposite sides into the slots 54 in the sleeve 16. The pins couple the first and second tube members together. A coil spring 65 is placed around the elongated shaft 12 within sleeve 16 and extends between bushing 30 and pins 63 to bias the coupling 18 toward the connector 20 and proximal end of the shaft 12. The coupling 18 is not free to rotate about the cannula but remains fixed in a preselected plane through the cannula.

Figure 7:
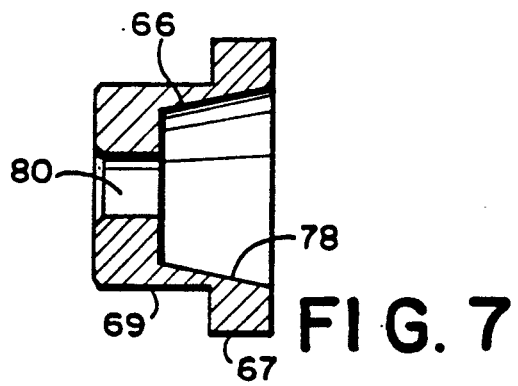
FIG. 7 is an enlarged cross sectional view of a retainer member portion of FIG. 6.
Figure 8:
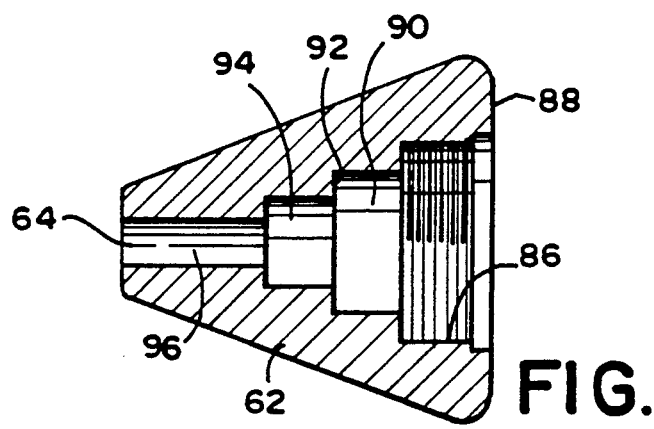
FIG. 8 is an enlarged cross sectional view of a conical member portion of FIG. 6.
Figure 6:
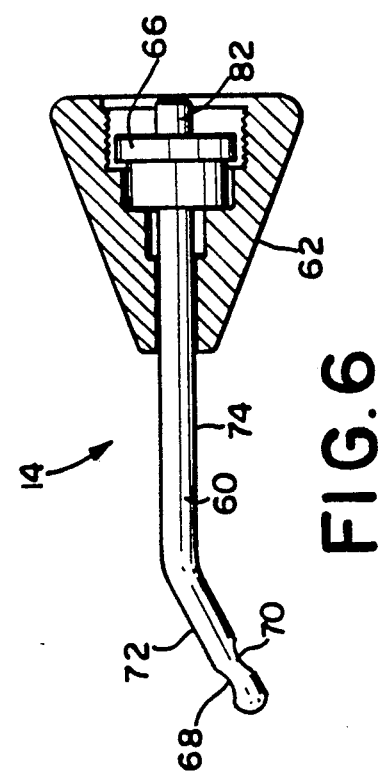
FIG. 6 is an enlarged elevational plan view, partially in cross section, of a shaft tip of the cannula of FIG. 1.

FIGS. 6 through 8 show the shaft tip 14 in more detail. The shaft tip 14 includes a shaft tip portion 60; a conical member 62 having a central passageway through which the shaft tip portion 60 is inserted; and a retainer member 66. The shaft tip portion 60 comprises a central lumen which opens to ambient atmosphere at the proximal end of the portion 60 and opens up to ambient atmosphere through side holes 68 and 70 near the opposite end of the portion 60. The shaft tip portion 60 includes a bent distal end portion 72 integrally formed with a straight portion 74.

The retainer member 66 is cylindrical in shape and comprises a larger diameter base portion 67 and smaller diameter distal portion 69. A conically shaped bore 78 is formed in the base portion 67 extending into the distal portion 69. The bore 78 is contiguous with and coaxial with a constant diameter smaller bore 80 through the distal portion of the retainer and open at the distal end. Bore 80 is just slightly larger than the diameter of shaft tip portion 60. The straight portion 74 of the shaft tip portion 60 is inserted through the bores 80 and 78 and retainer member 66 is attached to the straight portion 74 by soft solder. When attached, the straight portion extends proximally beyond the end of the retainer member 66 at 82.

The conical member 62 comprises an internally threaded bore 86 at the base 88 of the conical member. The diameter of the bore is large enough such that the internal threads of the bore 86 will mate with the external threads on annular ring 42 of the conical member connector 40 attached to shaft 12. The bore 86 communicates with an interior first smaller diameter cylindrical recess 90. Recess 90 is in turn in communication with cylindrical recess 94 which has a smaller diameter than recess 90. Internal annular shoulder 92 is formed at the interface between recess 90 and 94. Finally recess 94 communicates with bore 96 which opens to ambient atmosphere at the distal end of the conical member 62 opposite base 88. A passage 64 extends through the base 86, recess 90 and 94 and bore 96.

During assembly of the shaft tip 14, the shaft tip portion 60 is straight and the tip portion 60 with retainer member 66 attached is passed through the passageway 64 of the conical member. The diameter of the bore 96 is slightly larger than the diameter of the shaft tip portion 60 so that the conical member is freely rotatable about and slidable along the shaft tip portion 60. The distal end portion 72 is then bent to form an angle to the remaining straight portion 74 of the shaft tip portion 60. The conical member 62 is trapped between the bent portion 72 and the retainer member 66.

Referring to FIGS. 6, 7 and 8, when the conical member 62 is threaded onto annular ring 42 the distal portion 69 of retainer member 66 seats within recess 90 and engages annular shoulder 92. The width of the threaded bore 86 in the conical conical member is greater than the width of the base portion 67 on the retainer member so that the threads extend proximally beyond the base portion 67 to grab the threads on annular ring 42. The conically tapered end 44 of connector 23 mates with the conically shaped bore 78 in the retainer member while the proximally protruding portion 82 of the shaft tip portion 60 fits within the bore 46 in the connector 23.

FIG. 1 shows all of the components of FIGS. 1-8 assembled together. As such a lumen is provided which extends from the open end of connector 20 as follows: through the elongated shaft 12, which is coupled to the connector 20 when the tapered end 26 fits within the tapered base 21; through the connector 23, which receives end 28 of the elongated shaft 12 in bore 38 and which receives portion 82 of the shaft tip portion 60 in bore 46; and through the lumen in the shaft tip portion 60. The lumen opens to ambient atmosphere through holes 68 and 70 in the shaft tip portion. The lumen is substantially straight throughout the cannula along the cannula's longitudinal axis until the lumen reaches the bent portion 72 which is transverse to the longitudinal axis of the remainder of the cannula. In particular, the angle made by the transverse distal end portion of the shaft tip portion is preferably 27° which is established by the requirements of the human anatomy. Since the conical member 62 is free to rotate about the shaft tip portion 60 when the shaft tip 14 is attached to the connector 23 as described above, the angular orientation of the bent portion 70 about the longitudinal axis of the cannula can be set at any desired rotation. In other words, the angle that the bent portion makes with the longitudinal axis is fixed, preferably at 27°, but the bent portion can be rotated through 360° about the longitudinal axis before the shaft tip is attached to the elongated shaft.

Figure 9:
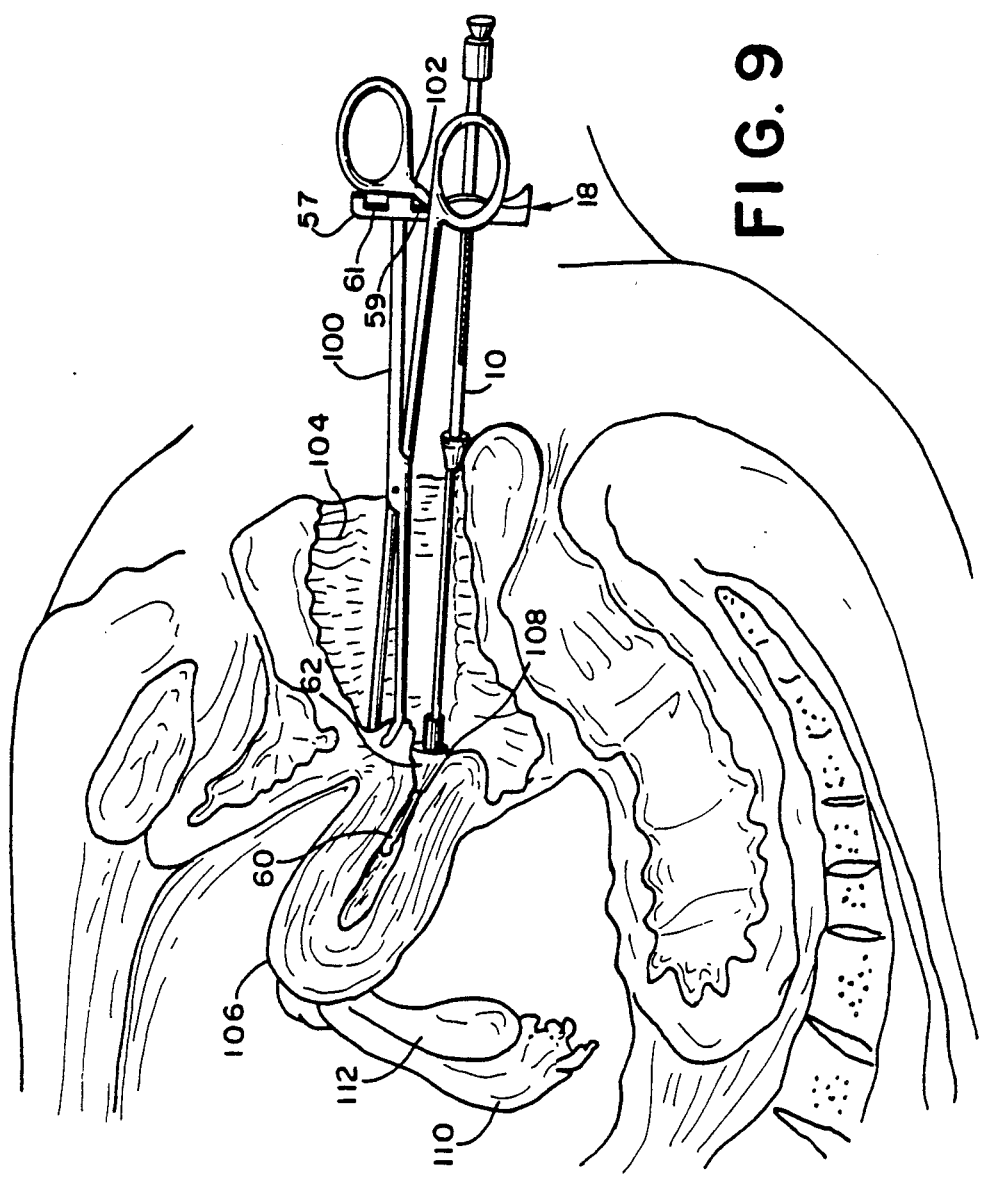
FIG. 9 is an artist's rendering in cross section of the human female adnexa and uterine vault showing the placement of the cannula of FIG. 1 in cooperation with a cervical tenaculum.

FIG. 9 is an artist's rendering of the female human anatomy showing in cross section the vagina 04, the uterus 106, cervix 108, ovaries 112 and fallopian tubes 110. During a laparoscopy an endoscope (not shown) is inserted through the interior abdominal wall through or adjacent to the umbilicus of the patient (at the top of the FIG.) to view the abdominal cavity including the adnexa. With the patient lying on her back as shown in FIG. 9, it is possible that the uterus 106 may block a clear view of the posterior side of the uterus, adnexa and the cul-de-sac. To move the uterus out of the way a tenaculum 100 is inserted through the vagina to seize the cervix anterior to the cervical as shown in FIG. 9.

As part of a laparoscopy procedure to examine the uterus etc., the cannula 10 is inserted posterior to the tenaculum through the cervical as with the tip portion 60 extending into the uterus. The conical member 62 engages the cervical as 108 to seal off the uterine cavity. To hold the cannula in place and apply pressure against the cervix the doctor places his fingers around the finger grip 22 and his thumb around the concave cut out 55 on the coupling member 18 and squeezes the coupling forward against the spring 65 until one of the slots 59 or 61 is in a position to engage the bridge between the ring handles of the tenaculum 100. When the doctor removes his hand from the cannula it is held in place against the tenaculum by the spring. It is very important that the transverse distal end portion 72 of the shaft tip portion 60 be pointing up at twelve o'clock relative to the longitudinal axis of the cannula, i.e. that the portion 72 be pointing up in the plane of the coupling 18. In this position when dye is forced through the lumen of the cannula from the connector 20 it will exit through the holes 68 and 70 in close proximity to the points where the fallopian tubes open into the uterus so that the dye will be forced through the fallopian tubes to be viewed through the laparoscope. The conical member 62 seals off the cervix so the dye will not find a path out of the uterus through the cervix.

If the bent portion of the tip 72 is not directed upward at twelve o'clock relative to rotation about the longitudinal axis then the holes 68 and 70 may be blocked by the uterine walls and the dye will not be forced into the fallopian tubes. To insure proper orientation, in the prior art, mating luer connectors were provided on the shaft tip and the distal end of the elongated shaft. The luer connectors are made of soft brass and with repeated use become stretched which causes misalignment of the bent tip. With the shaft tip portion 60 and connector 23 of the present invention, the proper orientation of the bent tip 72 can be adjusted as needed, eliminating any need to change the doctor's procedure. Hence, a universally interchangeable shaft and shift tip portion is provided and it is no longer necessary that tips be mated to shafts as was required in the prior art.

Figure 10:
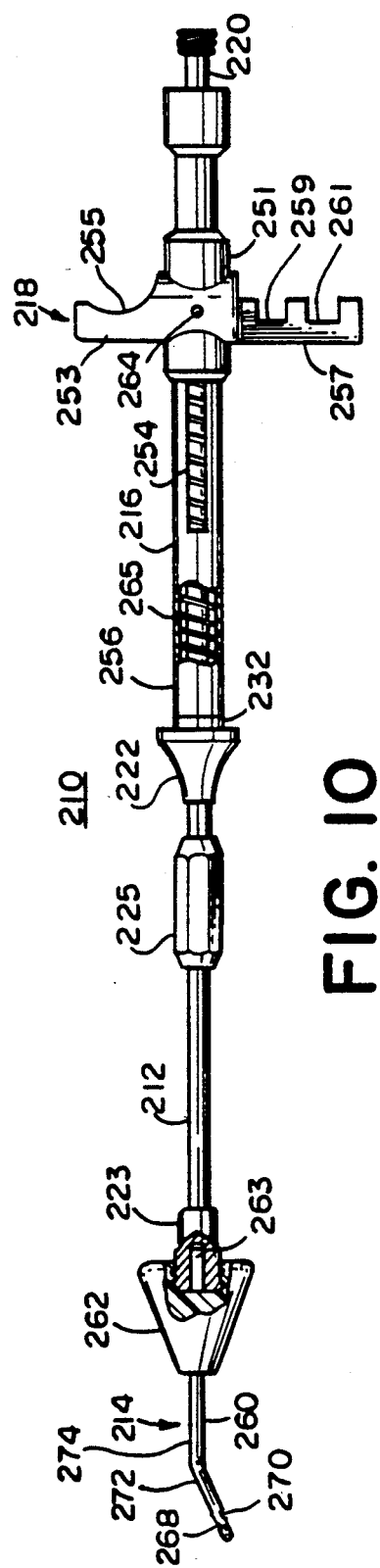
FIG. 10 is an elevational plan view, partially in cross section, of an alternate embodiment laparoscopy cannula of the present invention.
Figure 11:
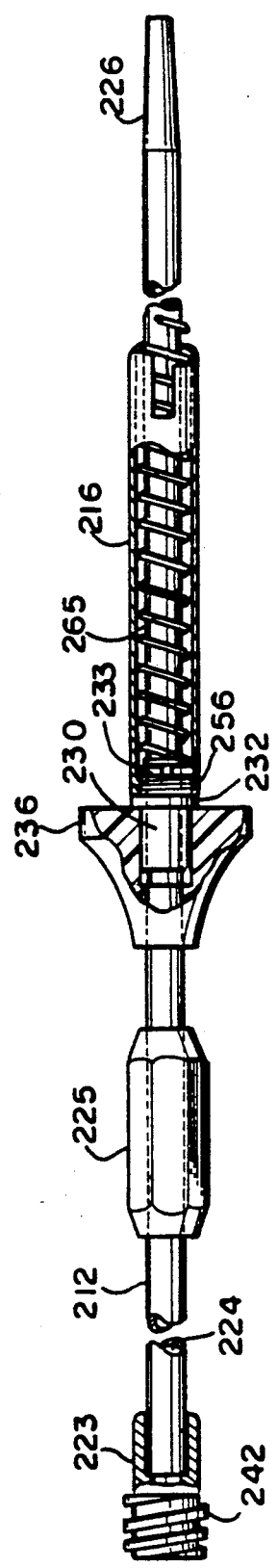
FIG. 11 is an enlarged elevational plan view, partially in cross section, of a portion of the cannula of FIG. 10.

Referring now to FIGS. 10 through 12, an alternate embodiment cannula designated generally 210 is shown having an elongated shaft 212, a shaft tip designated generally 214, sleeve 216, a coupler designated generally 218, proximal connector 220, curved finger grip 222, a distal connector 223 and an elongated finger grip 225. The shaft 212 is preferably made of stainless steel, cylindrical in shape, straight and includes a central lumen 224 which is open to ambient atmosphere at each end. End 226 is tapered.

FIG. 12 shows the shaft 212 with an annular stop washer 233 soft soldered to the elongated shaft in its medial portion. The elongated generally cylindrical finger grip 225 is coaxial with the elongated shaft and has a larger diameter. The elongated grip is soft soldered to the elongated shaft as well and is spaced apart distally from the washer 233. The elongated grip 225 has elongated concave cut outs 231 around the outer periphery of the grip 225 to make it easier to grip by the fingers.

FIG. 11 shows the shaft 212 of FIG. 12 with an annular stop ring 232 threaded onto the externally threaded bushing 230 which is coaxial with shaft 212 and slidably mounted thereon between ring 233 and elongated grip 225. The ring 232 is cemented in placed somewhere in the middle of the bushing 230. The concave curved, annularly shaped finger grip 222 has a center through hole large enough to accommodate the shaft 212 and is positioned on the shaft 212. An internally threaded bore within the base 236 of the curved finger grip 222 mates with the threads of the bushing 230. The curved grip 222 is threaded onto the bushing 230 from the distal end until it engages the stop ring 232 whereupon it is centered in place. The curved grip 222 is rotatable and slidable about shaft 212 with the bushing 230.

Referring to FIGS. 11 and 12, the connector 223 is a Luer Lok connector which is generally cylindrical in shape with an internal bore at its proximal end to receive the distal end of the elongated shaft 212 which is soft soldered in place. The Luer Lok threads 242 surround the outside of the distal end of the connector.

The shaft tip 214 includes a shaft tip portion 260; and a conical member 262. The shaft tip portion extends through the conical member 262 along the axis of the conical member. It protrudes proximally at 263. The shaft tip portion 260 comprises an internal lumen which opens to ambient atmosphere at its proximal end 263 and to ambient atmosphere distally through side holes 268 and 270. The shaft tip portion 260 includes a bent distal end portion 272 integrally formed until a straight portion 274.

The conical member 262 has an internally threaded proximal bore portion adapted to mate with the Luer Lok threads 242 on the connector 223. When the conical member 262 is threaded to the connector 223, the portion 263 communicates with the lumen of shaft 212. Because of the use of a Luer Lok connection and threads, the shaft tip 214 attains a single rotational orientation with respect to the shaft 212 like the prior art and unlike the embodiment shown in FIGS. 1-8.

The sleeve 216 is a straight, hollow metallic cylinder (stainless steel is preferred) having a pair of diametrically opposed, elongated slots 254. The internal diameter of the sleeve is constant and is large enough for the distal end of the sleeve 256 to extend over and beyond stop washer 233 and to thread onto the bushing 230 until the distal end of the sleeve 216 contacts the stop ring 232. The opposite end of sleeve 216 is inserted into a bore in the connector 220 and attached by soft solder. In the preferred embodiment, the connector 220 is a male Luer Lock connector. In a manner as shown in FIG. 5, the bore of the connector is in communication with a tapered interior bore portion which accepts the conically tapered end 226 of the shaft 212 when the sleeve is assembled over the shaft.

Referring to FIG. 10, the coupler 218 comprises a hollow cylindrical tube 251 through which the sleeve 216 is inserted. The tube passes through a hole in a second tube member 253 at right angles thereto. The second tube member 253 has a first portion with a concave cut out 255 which extends away from the first tube in a first direction and a flat portion 257 which extends away from the first tube in a second opposite direction from the first portion in a common plane therewith. The flat portion includes notches 259 and 261. Pins 264 extend through both the second and first tube members through opposite sides into the slots 254 in the sleeve 216. The pins couple the first and second tube members together. A coil spring 265 is placed around the elongated shaft 212 within sleeve 215 and extends between ring 233 and pins 264 to bias the coupling 218 toward the connector 220 and proximal end of the shaft 212.

FIG. 13 shows the spring 265 in more detail. The spring fixedly terminates at each end around a hollow truncated conical member 230 having an annular flat bushing surface 302. At one end the bushing surface 302 is in face to face contact with an annular bushing surface of the stop washer 233 and at the other end, against interiorly projecting portions of the pins 264.

When the various parts of the alternate embodiment 210 are assembled together as shown in FIG. 10 a cannula is provided having a lumen which extends from the open end of connector 220 through the elongated shaft 212, through the connector 223 and the shaft tip portion 260 including straight section 274 and bent portion 272. The cannula is used in the same manner as the cannula 10 as described in connection with FIG. 9, but the means for preserving the orientation of distal tip of the cannula relative to the plane of the coupling 218 even after multiple uses of the instrument is different. Instead of coupling the shaft tip 214 in the manner described for FIGS. 1-8, tip 214 is connected to the elongated shaft 212 in the conventional manner using a luer thread connection, however, the bushing 230 and shaft 212 are free to rotate relative to one another unlike the bushing 30 and shaft 12. The sleeve 216 with coupling 218 is attached to the shaft 212 by threading the sleeve onto the bushing 230 which is captured on shaft 212 between annular washer 232 and grip 225. After the cannula is assembled the orientation of the tip 214 can be aligned rotationally with respect to plane of the coupling 218 by gripping the grip 225 with one hand while holding the coupling and grip 222 in the other. The end surface of bushing 230 will act as a bearing surface against an annular surface of annular washer 233. The surface 302 will bear against the opposite side of washer 233 and rotate with respect thereto. Hence, a cannula is provided which has a tip portion coupled to the cannula with a standard luer fitting but which overcomes the problem of the prior art cannulas.

What is claimed is:

1. A cannula for use in laparoscopy comprising:
   an elongated shaft with a lumen therethrough along the longitudinal axis of said elongated shaft;
   a shaft tip for coupling to the distal end of said elongated shaft and separable therefrom, said shaft tip having a lumen in communication with the lumen of said elongated shaft and at least one opening in said shaft tip whereby said tip lumen communicates with ambient atmosphere, said tip having a distal end portion transverse to the longitudinal axis of said shaft, said tip further comprising a conical member disposed along said shaft tip proximally of said transverse distal end portion for engagement with the cervix of the uterus; and means for attaching the shaft tip to said elongated shaft such that said transverse distal end portion can be aligned and fixed at any rotational angle about the longitudinal axis of said elongated shaft.

2. The cannula of claim 1 wherein said conical member is freely rotatable about said shaft tip and comprises an internal threaded region at its base; and said elongated shaft comprises an external threaded portion on its distal end for mating with the internal threaded portion of said conical member.

3. The cannula of claim 2 wherein said cannula comprises a retainer member attached to the proximal end of said shaft tip for retaining said conical member along said shaft tip between said transverse distal end portion and said proximal end, said retainer member adapted to fit within a recessed cavity within said conical member distally of at least a portion of said interior threaded portion; said distal end of said elongated shaft having a conical taper for mating engagement with a conically shaped recess in said retainer member when said shaft tip is coupled to said elongated shaft.

4. The cannula of claim 3 wherein said cannula comprises a conical member connector having:
a proximal body portion with a central lumen for receiving the distal end of said elongated shaft; a distal end comprising said conical taper and having a central lumen in communication with the lumen of said elongated shaft when inserted in said body portion; and an enlarged annular region of greater diameter than said distal end of body portion, intermediate said body portion and conically shaped distal portion comprising said external threaded portion.

5. The cannula of claim 4 wherein the proximal end of said shaft tip extends through said retainer member for insertion in said central lumen in said conically tapered distal end whereby said lumen in said transverse distal end portion of said shaft tip is in communication with said lumen in said elongated shaft through said conical member connector.

6. The cannula of claim 1 wherein said cannula is intended for use with a cervical tenaculum and said cannula further comprises:
coupling means movable along at least a portion of said elongated shaft within a plane through said elongated shaft for engaging the cervical tenaculum and fixing said cannula at a preselected orientation to the tenaculum.

7. The cannula of claim 6 wherein said cannula comprises:
a connector coupled to the proximal end of said shaft for coupling said shaft lumen to an external fluid supply source.

8. The cannula of claim 6 wherein said cannula further comprises a slotted elongated cylindrical sleeve having a connector attached at its proximal end, said sleeve disposed to receive the proximal end of said elongated shaft, said shaft having an annular curved finger grip connected to the intermediate portion of said elongated shaft at the distal end of said sleeve, said coupling means comprising a cylindrical ; portion coaxial with said sleeve and disposed to move back and forth along said sleeve over said slotted region, said coupling means being biased proximally by a spring means.

9. A cannula for use with a cervical tenaculum in laparoscopy comprising:
an elongated shaft with a lumen therethrough along the longitudinal axis of said elongated shaft;
a shaft tip for coupling to the distal end of said elongated shaft and separable therefrom, said shaft tip having a lumen in communication with the lumen of said elongated shaft and at least one opening in said shaft tip whereby said tip lumen communicates with ambient atmosphere, said tip having a distal end portion transverse to the longitudinal axis of said shaft, said tip further comprising a conical member disposed along said shaft tip proximally of said transverse distal end portion for engagement with the cervix of the uterus; coupling means movable along at least a portion of said elongated shaft within a plane through said elongated shaft for engaging the cervical tenaculum at a preselected orientation to the tenaculum; and
means for aligning the transverse distal end portion in a plane at any rotational angle with respect to the plane of movement of said coupling means.

10. The cannula of claim 9 wherein said cannula comprises an annular washer fixed to the medial portion of said elongated shaft, an annular curved finger grip means rotatably mounted on said elongated shaft between said shaft tip and said annular washer, and an elongated cylindrical sleeve disposed to receive at its distal end, the proximal end of said elongated shaft and disposed to be attached to said annular curved finger grip at its distal end, said coupling means being coupled to said sleeve, said elongated shaft with attached transverse distal end portion being rotatable relative to said sleeve and coupling means.

11. The cannula of claim 10 wherein said coupling means is disposed to move back and forth along said sleeve and is biased proximally by a spring means.

12. The cannula of claim 11 wherein the sides of said annular washer comprise bearing surfaces against which said spring and said annular grip means are disposed to rotate when said elongated shaft is rotated relative to said coupling means.

13. The cannula of claim 10 wherein said cannula further comprises an elongated finger grip coaxial with said elongated shaft and fixedly attached thereto between said curved finger grip means and said shaft tip.

* * * * *